United States Patent
Sasaki et al.

(10) Patent No.: US 11,953,491 B2
(45) Date of Patent: Apr. 9, 2024

(54) DETECTION DEVICE

(71) Applicant: KELK Ltd., Hiratsuka (JP)

(72) Inventors: Kazuji Sasaki, Yokohama (JP);
Tomonori Murata, Yokohama (JP);
Daisuke Goto, Naka-gun (JP)

(73) Assignee: KELK Ltd., Hiratsuka (JP)

( * ) Notice: Subject to any disclaimer, the term of this patent is extended or adjusted under 35 U.S.C. 154(b) by 540 days.

(21) Appl. No.: 17/285,501

(22) PCT Filed: Oct. 8, 2019

(86) PCT No.: PCT/JP2019/039582
§ 371 (c)(1),
(2) Date: Apr. 15, 2021

(87) PCT Pub. No.: WO2020/080174
PCT Pub. Date: Apr. 23, 2020

(65) Prior Publication Data
US 2021/0382031 A1    Dec. 9, 2021

(30) Foreign Application Priority Data

Oct. 17, 2018  (JP) .................................. 2018-196049

(51) Int. Cl.
*G01N 21/59* (2006.01)
*G01N 21/94* (2006.01)
(Continued)

(52) U.S. Cl.
CPC ......... *G01N 33/2888* (2013.01); *G01N 21/59* (2013.01); *G01N 21/94* (2013.01);
(Continued)

(58) Field of Classification Search
CPC .... G01N 33/2888; G01N 21/94; G01N 21/59; H01Q 13/10; H01Q 1/2208; H01Q 1/38
See application file for complete search history.

(56) References Cited

U.S. PATENT DOCUMENTS 6,816,120 B2 * 11/2004 Kuramoto ............... H01Q 3/12
                                                      343/702
7,845,616 B2 * 12/2010 Hatsuzawa .......... G01D 5/2073
                                                      137/554
(Continued)

FOREIGN PATENT DOCUMENTS

CN    101162155 A    4/2008
CN    108463694 A    8/2018
(Continued)

OTHER PUBLICATIONS

Jiang Yu-lei et al., "Research on On-line Monitoring System of Partial Discharge for Gas Insulated Switchgear," China Academic Journal Electronic Publishing House, vol. 24(2), May 28, 2002, pp. 15-16 and English abstract thereof. (cited in the Jan. 20, 2023 Office Action issued for CN201980068486.3).

(Continued)

*Primary Examiner* — Hai V Nguyen
(74) *Attorney, Agent, or Firm* — Locke Lord LLP

(57) ABSTRACT

A detection device that is capable of being attached to a through hole includes a main body portion, a detection portion, a cover portion, an insulation portion, and an oscillation portion. The main body portion has an insertion portion and a head portion. The detection portion is arranged in the insertion portion and detects the state of a fluid. The cover portion is arranged so as to form a gap with the head portion. The insulating portion has a lateral wall having a cylindrical shape. An oscillation portion is accommodated inside the insulation portion, and performs a wireless output of a detection result of the detection portion by using the head portion, the cover portion and the gap as a slot antenna.

7 Claims, 8 Drawing Sheets

(51) Int. Cl.
  *G01N 33/28* (2006.01)
  *H01Q 1/22* (2006.01)
  *H01Q 1/38* (2006.01)
  *H01Q 13/10* (2006.01)

(52) U.S. Cl.
  CPC ............ *H01Q 1/2208* (2013.01); *H01Q 1/38* (2013.01); *H01Q 13/10* (2013.01)

(56) References Cited

U.S. PATENT DOCUMENTS

| | | | | |
|---|---|---|---|---|
| 8,640,940 | B2* | 2/2014 | Ohdaira | A61B 17/115 227/19 |
| 9,764,793 | B2* | 9/2017 | Murakami | F16F 9/465 |
| 10,801,958 | B2* | 10/2020 | Goto | H10N 10/17 |
| 11,326,913 | B2* | 5/2022 | Hocker | G01F 1/3259 |
| 2002/0158807 | A1* | 10/2002 | Kuramoto | H01Q 3/12 343/792 |
| 2007/0018849 | A1 | 1/2007 | Salser, Jr. | |
| 2008/0062059 | A1* | 3/2008 | Freni | H01Q 15/002 343/909 |
| 2008/0087858 | A1* | 4/2008 | Hatsuzawa | F02D 9/105 324/207.16 |
| 2010/0101728 | A1 | 4/2010 | Iwasaki | |
| 2011/0080161 | A1 | 4/2011 | Maruyama et al. | |
| 2011/0095067 | A1* | 4/2011 | Ohdaira | A61B 17/07207 606/49 |
| 2013/0099991 | A1* | 4/2013 | Wright | B23P 11/005 29/505 |
| 2014/0240856 | A1* | 8/2014 | Allore | H04M 1/0266 264/1.24 |
| 2014/0267896 | A1* | 9/2014 | Cox | H04N 5/63 348/383 |
| 2015/0201808 | A1* | 7/2015 | Katsuki | A23N 1/02 241/199.12 |
| 2016/0288867 | A1* | 10/2016 | Murakami | B62J 45/42 |
| 2018/0026353 | A1* | 1/2018 | Tseng | H01Q 13/10 455/575.7 |
| 2018/0062244 | A1* | 3/2018 | Huang | H01Q 5/371 |
| 2018/0360271 | A1* | 12/2018 | Katsuki | A47J 43/0766 |
| 2019/0000272 | A1* | 1/2019 | Katsuki | A23N 1/02 |
| 2019/0128807 | A1* | 5/2019 | Goto | G01N 21/59 |
| 2020/0194868 | A1* | 6/2020 | Maruyama | H01Q 1/12 |
| 2020/0194883 | A1* | 6/2020 | Maruyama | H01Q 1/1221 |
| 2020/0271489 | A1* | 8/2020 | Hocker | G01F 1/3266 |

FOREIGN PATENT DOCUMENTS

| | | |
|---|---|---|
| JP | S59-055604 A | 3/1984 |
| JP | H04-004725 A | 1/1992 |
| JP | 2006-286269 A | 10/2006 |
| JP | 2016-196087 A | 11/2016 |
| WO | 2017/187967 A1 | 11/2017 |

OTHER PUBLICATIONS

Qin Ming et al., "Petroleum Instruments" No. 02, Development of 1.1GHz Electromagnetic Wave Propagation Logging Tool, China Academic Journal Electronic Publishing House, vol. 16(2), Apr. 30, 2002, pp. 7-9 and English abstract thereof. (cited in the Jan. 20, 2023 Office Action issued for CN201980068486.3).
International Search Report dated Dec. 17, 2019, issued for PCT/JP2019/039582 and English translation thereof.

* cited by examiner

DETECTION DEVICE

TECHNICAL FIELD

The present invention relates to a detection device.

Priority is claimed on Japanese Patent Application No. 2018-196049, filed Oct. 17, 2018, in Japan, the content of which is incorporated herein by reference.

BACKGROUND ART

Patent Literature 1 discloses a detection device that detects the deterioration of a lubricating oil of a machine. The detection device disclosed in Patent Document 1 includes a fixing member having a bolt shape. A screw portion of the fixing member is formed with a groove constituting an oil intrusion space for intruding lubricating oil into the tip surface thereof. The screw portion of the detection device is attached to a screw hole of machinery that allows the lubricating oil flow path to communicate with the outside. By attaching the screw portion to the screw hole, the groove of the above-described screw portion is disposed in the lubricating oil flow path of the machinery so that the lubricating oil enters the groove. The detection device optically detects impurities contained in the lubricating oil that has entered the groove using a light-emitting element and a light-receiving element.

CITATION LIST

Patent Literature

[Patent Document 1] Japanese Unexamined Patent Application Publication No. 2016-196087

DISCLOSURE OF INVENTION

Technical Problem

The detection device disclosed in Literature 1 wirelessly outputs a detection result. However, since the detection device of Patent Document 1 incorporates an antenna, the size of a portion protruding from the outer surface of the machinery increases, and there is a possibility that the flexibility of installation of the detection device decreases. The present invention is made in view of such problems and the object of the present invention is to provide a detection device capable of preventing a decrease in installation flexibility while wirelessly outputting a detection result.

Solution to Problem

A detection device according to an aspect of the present invention is a detection device that is capable of being attached to a through hole, including: a main body portion including an insertion portion that is capable of being disposed inside the through hole and a head portion that is disposed outside the through hole when the insertion portion is disposed inside the through hole; a detection portion disposed in the insertion portion and configured to detect a state of a fluid; a cover portion disposed so as to form a gap between the cover portion and the head portion; an insulating portion disposed so as to be sandwiched between the head portion and the cover portion; and an oscillation portion accommodated inside the insulating portion and configured to perform wireless output of a detection result of the detection portion using the head portion, the cover portion, and the gap as a slot antenna.

Advantageous Effects of Invention

According to the present invention, it is possible to prevent a decrease in installation flexibility while wirelessly outputting a detection result.

MODE FOR CARRYING OUT THE INVENTION

First Embodiment

Hereinafter, a first embodiment of the present invention will be described in detail with reference to FIG. 1 to FIG. 2.

<Detection Device>

A detection device 1A according to the present embodiment is attached to machinery such as a work machine, and detects states of various fluids such as lubricating oil and working fluid of the machinery.

Figure 1:
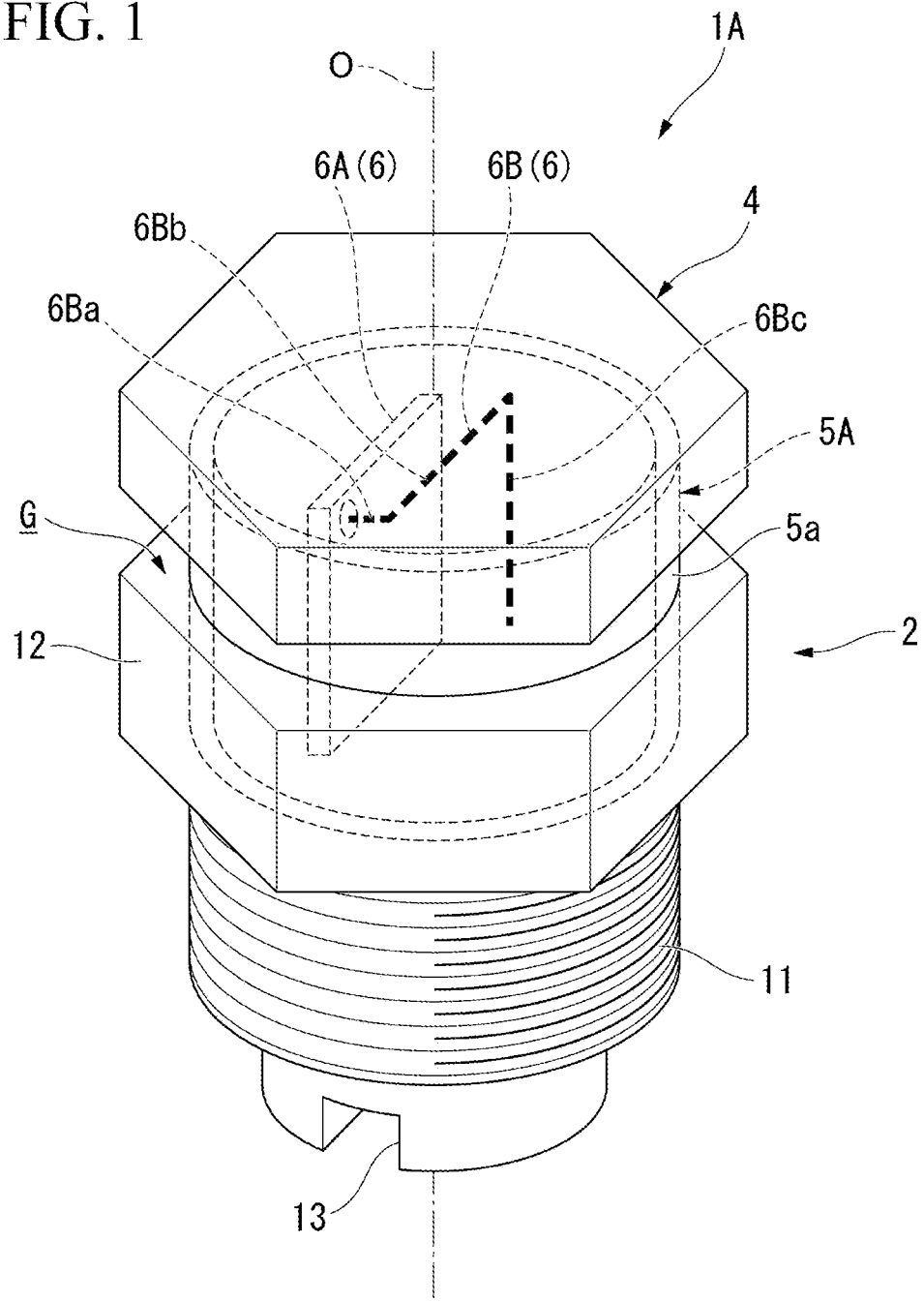
FIG. 1 is a perspective view showing a schematic configuration of a detection device according to a first embodiment of the present invention.
Figure 2:
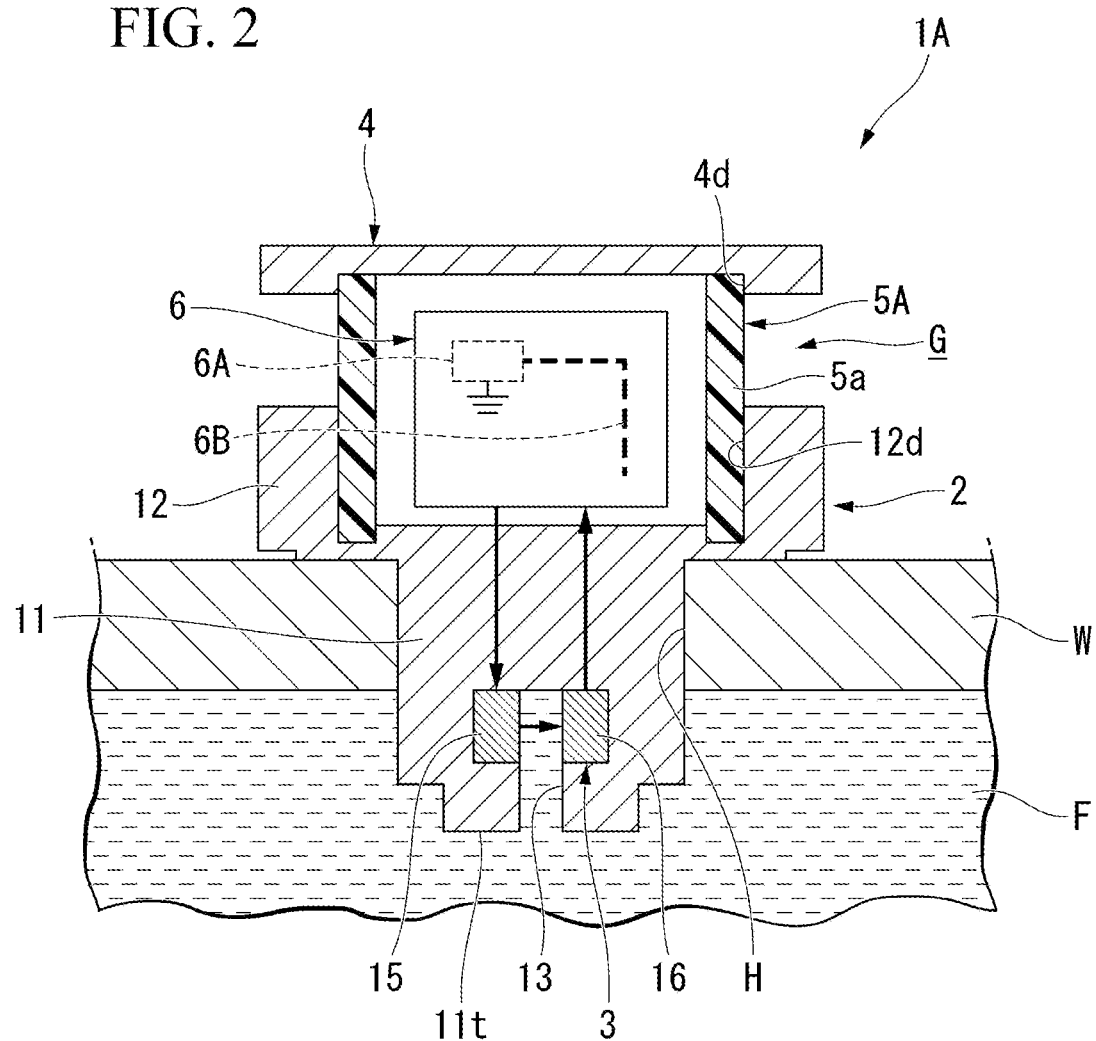
FIG. 2 is a cross-sectional view of the detection device according to the first embodiment of the present invention.

As shown in FIG. 1 and FIG. 2, the detection device 1A is capable of being attached to a through hole H communicating with the flow path of the fluid F. The through hole H is formed in a wall portion W of, for example, a gearbox, a transaxle, and piping of a hydraulic system. The through hole H of the present embodiment is a round hole, and a female screw (not shown) is formed on the inner peripheral surface thereof.

The detection device 1A includes a main body portion 2, a detection portion 3, a cover portion 4, an insulating portion 5A, and an oscillation portion 6.

The main body portion 2 includes an insertion portion 11 and a head portion 12. The main body portion 2 shown in the present embodiment has a similar shape to a bolt.

The insertion portion 11 is formed so as to be capable of being disposed inside the through hole H. The insertion portion 11 of the present embodiment is formed in a cylindrical shape, and a male screw that is capable of being fastened to the female screw of the through hole H by a screw action is formed on an outer peripheral surface of the insertion portion 11. A recessed portion 13 having a groove shape and being capable of accommodating the fluid F is formed on an end portion of the insertion portion 11. The recessed portion 13 is recessed in a direction approaching the head portion 12 from an end surface 11t on a side opposite to the head portion 12. When the detection device 1A is attached to the through hole H, the fluid F to be detected flows into the recessed portion 13.

The head portion 12 is disposed outside the through hole H when the insertion portion 11 is disposed inside the through hole H. The head portion 12 of the present embodiment corresponds to a head part of a hexagonal bolt. That is, the cross-sectional contour of the head portion 12 perpendicular to the axial line O is hexagonal. The diameter of an inscribed circle of the hexagon of the head portion 12 is larger than an outer diameter of the insertion portion 11. By turning the head portion 12 with a tool such as a spanner, the insertion portion 11 is capable of being screwed into or loosened from the through hole H.

The detection portion 3 is disposed in the insertion portion 11 and detects the state of the fluid F. The detection portion 3 illustrated in the present embodiment is formed of a so-called optical sensor including a light-emitting element 15 and a light-receiving element 16. The light-emitting element 15 and the light-receiving element 16 are arranged to face each other in a direction intersecting with the axial line of the insertion portion 11 with the recessed portion 13 interposed therebetween. Of light emitted from the light-emitting element 15, light reaching the light-receiving element 16 is converted into an electric signal by the light-receiving element 16. The converted electric signal is output from the light-receiving element 16 to the oscillation portion 6. Here, since the electric signal corresponding to the amount of the light is correlated with, for example, the amount of impurities contained in the fluid F, the state of the fluid F is capable of being determined by analyzing the electric signal output from the light-receiving element 16. In addition, the state of the fluid F is capable of being obtained by using a map, a table, an equation, or the like, of the peak value, the integrated value, or the like, of the electric signal and the amount of impurities contained in the fluid F obtained in advance by simulation, experiment, or the like.

The cover portion 4 is disposed so as to form a gap G between the cover portion 4 and the head portion 12. A cross-sectional contour of the present embodiment perpendicular to the axial line O of the cover portion 4 is a hexagon congruent with the cross-sectional contour of the head portion 12, and the positions of the top portions of the cover portion 4 and the head portion 12 coincide with each other in the circumferential direction about the axial line O as viewed from the axial line O direction. Therefore, a tool such as a ring wrench is capable of being easily fitted to the head portion 12 through the cover portion 4. The cover portion 4 and the head portion 12 in the embodiment are made of a metallic material. The thickness along the axial line O of the cover portion 4 in the present embodiment is smaller than the thickness of the head portion 12.

The insulating portion 5A is disposed so as to be sandwiched between the head portion 12 and the cover portion 4. The insulating portion 5A has a lateral wall 5a having a cylindrical shape. The insulating portion 5A in the present embodiment is formed in a cylindrical shape. The insulating portion 5A is formed of an insulating material having excellent insulating properties. Examples of the insulating material constituting the lateral wall 5a include ceramics and synthetic resins. Examples of the synthetic resins include polyphenylene sulfide. Here, the head portion 12 and the cover portion 4 of the present embodiment are provided with accommodation recesses 4d and 12d that have a circular shape and that accommodate an end portion of the insulating portion 5A, on opposing surfaces facing each other. Both end portions of the insulating portion 5A in the axial line O direction are accommodated and fixed in the accommodation recess 4d of the cover portion 4 and the accommodation recess 12d of the head portion 12. The insulating portion 5A is exposed outward in the circumferential direction about the axial line O via the gap G.

The oscillation portion 6 is accommodated inside the insulating portion 5A. The oscillation portion 6 performs wireless output of a detection result of the detection portion 3 using the head portion 12, the cover portion 4, and the gap G as a slot antenna. The oscillation portion 6 in the present embodiment includes a circuit board portion 6A including a wireless communication circuit (not shown) and a wire antenna portion 6B electrically connected to the wireless communication circuit in the circuit board portion 6A. An electric signal is input to the circuit board portion 6A from at least the light-receiving element 16 of the detection portion 3. The circuit board portion 6A in the present embodiment has, for example, a circuit that operates the light-emitting element 15 of the detection portion 3 based on a received signal by wireless communication. In the present embodiment, a small battery (not shown) is provided to supply power to the wireless communication circuit and the detection portion 3. In addition, for example, a loop antenna or the like may be provided, and electromotive force generated in the loop antenna or the like may be used as power for driving the wireless communication circuit.

The circuit board portion 6A is formed in a rectangular flat plate shape extending in the axial line O. The wire antenna portion 6B is connected to the vicinity of one of two corners of the circuit board portion 6A on the side closer to the cover portion 4. The wire antenna portion 6B includes a first part 6Ba, a second part 6Bb, and a third part 6Bc. The first part 6Ba extends linearly in a direction away from the circuit board portion 6A. The second part 6Bb linearly extends from an end portion of the first part 6Ba along a side of the circuit board portion 6A closer to the cover portion 4. The third part 6Bc linearly extends from an end portion of the second part 6Bb toward the head portion 12. In other words, the second part 6Bb and the third part 6Bc extend in a direction perpendicular to the first part 6Ba, and the third part 6Bc extends in a direction perpendicular to the second part 6Bb.

The oscillation portion 6 is capable of generating an electric field between the head portion 12 and the cover portion 4 by emitting radio waves from the wire antenna portion 6B. That is, by emitting radio waves from the wire antenna portion 6B, radio waves are propagated from the wire antenna portion 6B to the outside through the gap G, and the head portion 12, the cover portion 4, and the gap G function as a slot antenna; thus, radio waves are emitted from the slot antenna. The size of the gap G in the axial line O direction is set to a sufficiently small value with respect to wavelengths X, of transmission frequencies (for example, 2.4 GHz) used in wireless communication, and can be set to be, for example, substantially 2120.

<Operation and Effects>

In the detection device 1A described above, since the head portion 12 and the cover portion 4 are electrically insulated from each other by the insulating portion 5A, the head portion 12, the cover portion 4, and the gap G can function as a slot antenna. Therefore, it is possible to perform wireless output of the detection result of the detection portion 3 using the slot antenna formed by the head portion 12, the cover portion 4, and the gap G. Therefore, it is possible to prevent an increase in size of a protruding portion of the detection device 1A from the machinery. Therefore, it is possible to prevent a decrease in installation flexibility of the detection device 1A while wirelessly outputting the detection result.

Further, since the oscillation portion 6 includes the wire antenna portion 6B, it is also possible to directly perform wireless output from the wire antenna portion 6B through the gap G together with wireless output by the slot antenna.

Second Embodiment

Figure 3:
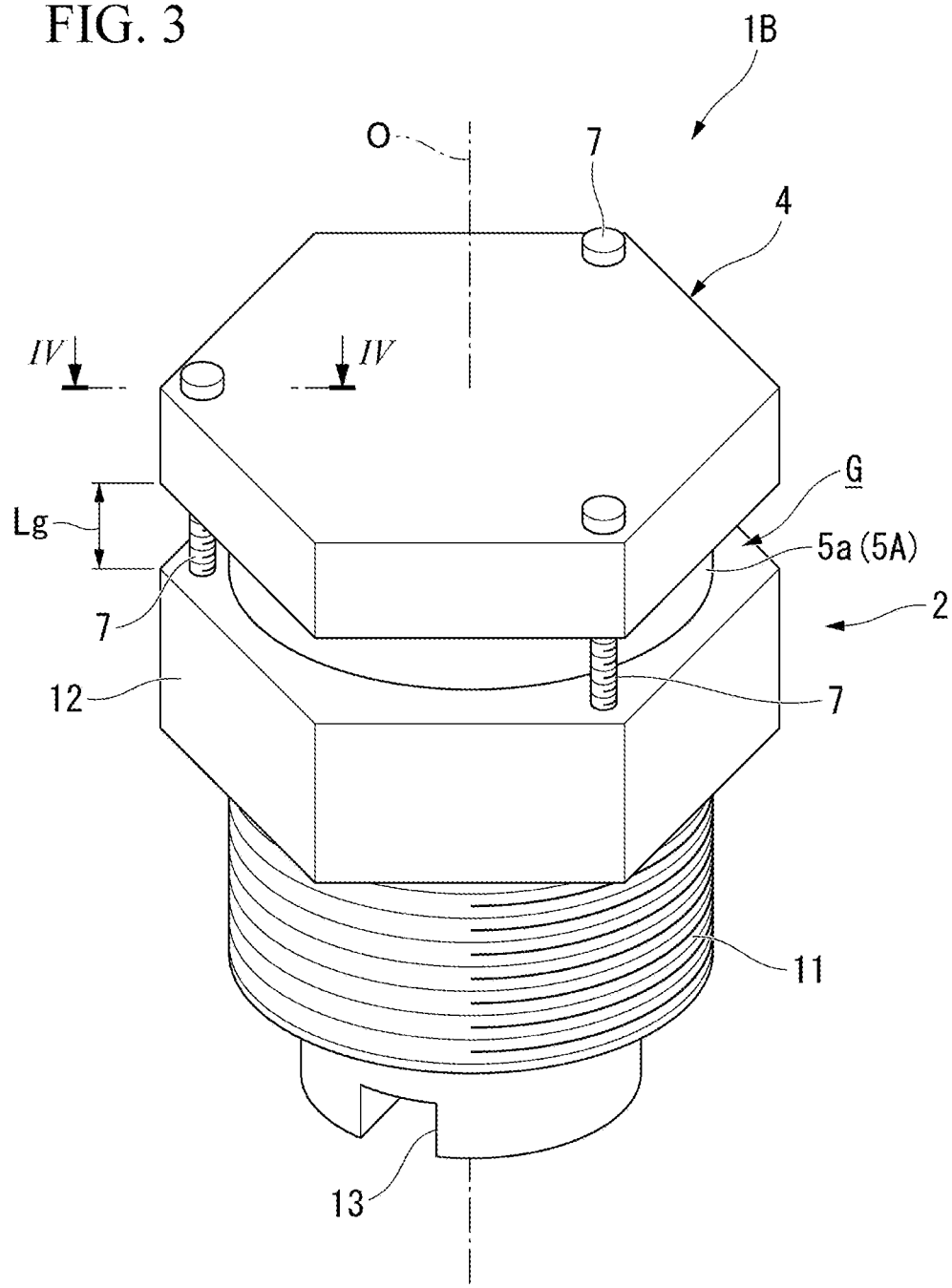
FIG. 3 is a perspective view showing a schematic configuration of a detection device according to a second embodiment of the present invention.
Figure 4:
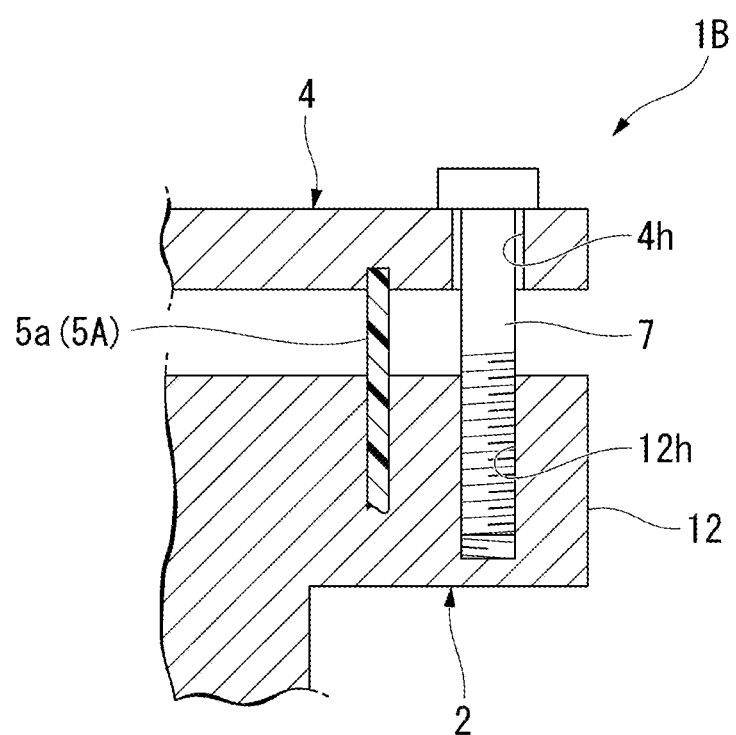
FIG. 4 is a cross-sectional view taken along line IV-IV of FIG. 3.

Next, a second embodiment of the present invention will be described with reference to FIG. 3 and FIG. 4. In FIG. 3 and FIG. 4, components similar to those of the first embodiment are denoted by the same reference signs, and detailed description thereof is omitted.

The detection device 1B of the second embodiment includes a main body portion 2, a detection portion 3 (see FIG. 2), a cover portion 4, an insulating portion 5A, an oscillation portion 6 (see FIG. 2), and a conductor portion 7.

The main body portion 2 includes an insertion portion 11 and a head portion 12. The main body portion 2 has the same configuration as the first embodiment and has a similar shape to a bolt.

The head portion 12 has a screw hole 12h on a surface facing the cover portion 4. The screw hole 12h in the present embodiment extends in the axial line O direction. The screw hole 12h is formed in the vicinity of a corner of the hexagon of the head portion 12. The head portion 12 of the present embodiment has three screw holes 12h. These three screw holes 12h are formed such that the intervals between adjacent screw holes 12h are equal in the circumferential direction about the axial line O. The present embodiment shows a case where the screw holes 12h are formed at every 120 degrees about the axial line O.

The cover portion 4 has a loose insertion hole 4h at a position facing the screw hole 12h formed in the head portion 12. The loose insertion hole 4h has an inner diameter that is slightly larger than an inner diameter of the screw hole 12h. Three loose insertion holes 4h are formed in the present embodiment. That is, these three loose insertion holes 4h are also formed at every 120 degrees around the axial line O so that the intervals between the loose insertion holes 4h adjacent to each other in the circumferential direction about the axial line O are equal.

The conductor portion 7 is disposed so as to extend between the main body portion 2 and the cover portion 4. Specifically, it is disposed so as to extend between the head portion 12 and the cover portion 4. In the present embodiment, three conductor portions 7 are provided as a plurality of conductor portions 7. The three conductor portions 7 are disposed outward of the insulating portion 5A in a radial direction about the axial line O. The three conductor portions 7 define the gap G in the circumferential direction about the axial line O. Part of each of the conductor portions 7 disposed in the gap G is formed in a cylindrical shape.

Figure 5:
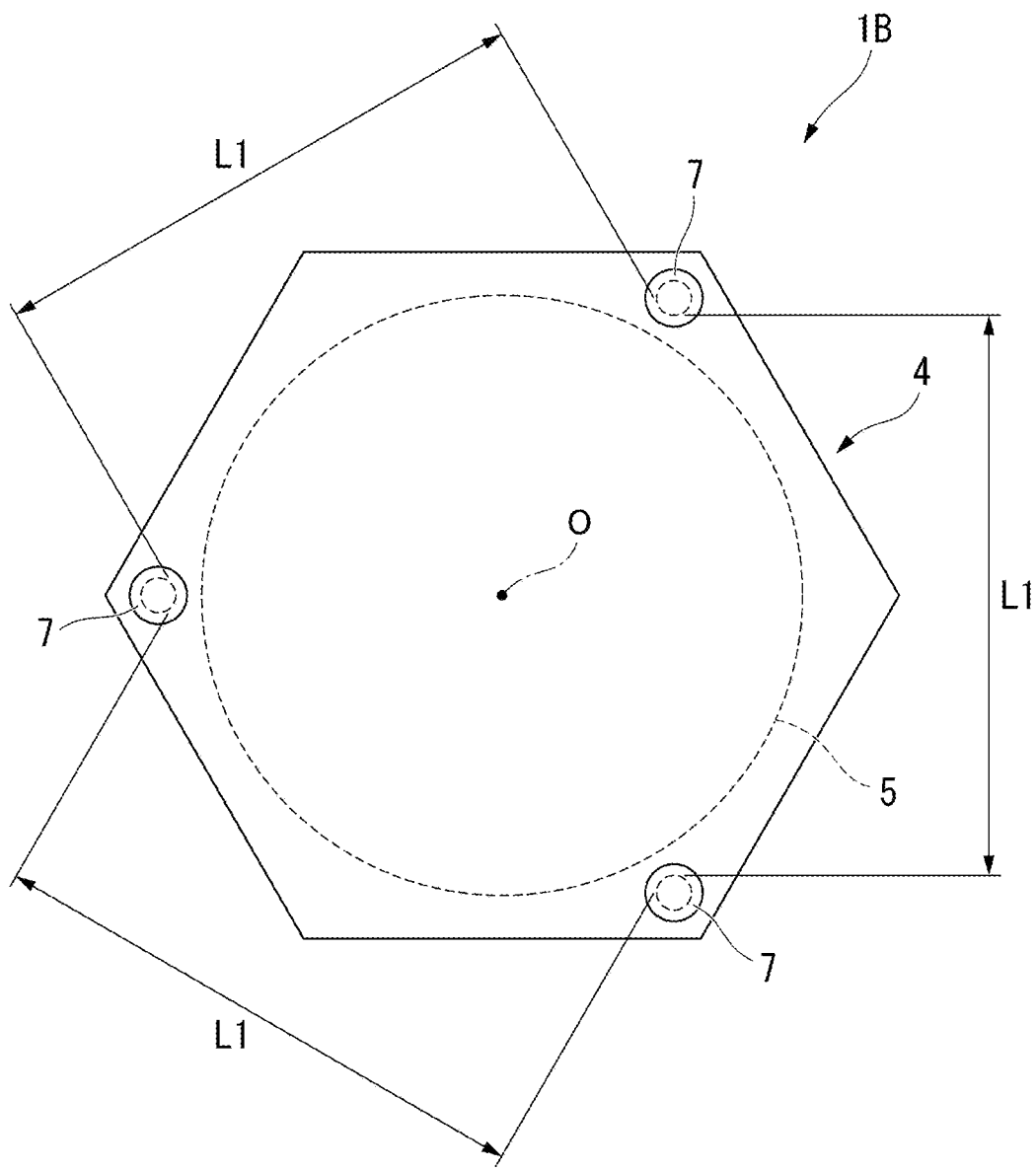
FIG. 5 is a plan view showing an arrangement of conductor portions of the detection device according to the second embodiment of the present invention.

A screw can be used as the conductor portion 7 in the present embodiment. The cover portion 4 and the main body portion 2 are connected to each other in the axial line O direction by screwing each of the conductor portions 7 formed of a screw into the screw hole 12h of the head portion 12 through the loose insertion hole 4h of the cover portion 4. The conductor portions 7 formed of a screw are made of metal and electrically connect the cover portion 4 and the head portion 12. As shown in FIG. 5, the three conductor portions 7 are arranged at intervals of 120 degrees around the axial line O. That is, the intervals between the conductor portions 7 in the circumferential direction around the axial line O are equal.

The linear distances L1 between the conductor portions 7 adjacent to each other in the circumferential direction are $\lambda/4$ with respect to wavelengths $\lambda$ of transmission frequencies used in wireless communication. These conductor portions 7 constitute three slot antennas together with the head portion 12, the cover portion 4, and the gap G. The long-side direction of each of these three slot antennas is perpendicular to the axial line O. The linear distance L1 is not limited to being strictly equal to "$\lambda/4$". There may be tolerances or differences having the same function, such as $(\lambda/4)\pm5\%$.

Operation and Effects of Second Embodiment

In the detection device 1B, by providing the plurality of conductor portions 7, a plurality of slot antennas having the same shape are capable of being formed by arranging in the circumferential direction about the axial line O. Therefore, it is possible to uniformly perform wireless output in the circumferential direction about the axial line O. As a result, even in a work machine in which relative positions of the oscillation portion and the receiver change during operation, stable output transmission and reception are possible. In addition, it is not necessary to attach the detection device 1B at a specific position in the circumferential direction.

Further, since the linear distance L1 between the conductor portions 7 adjacent to each other in the circumferential direction is set to $\lambda/4$, the antenna gain is capable of being improved over the entire circumference.

First Modification of Second Embodiment

Figure 6:
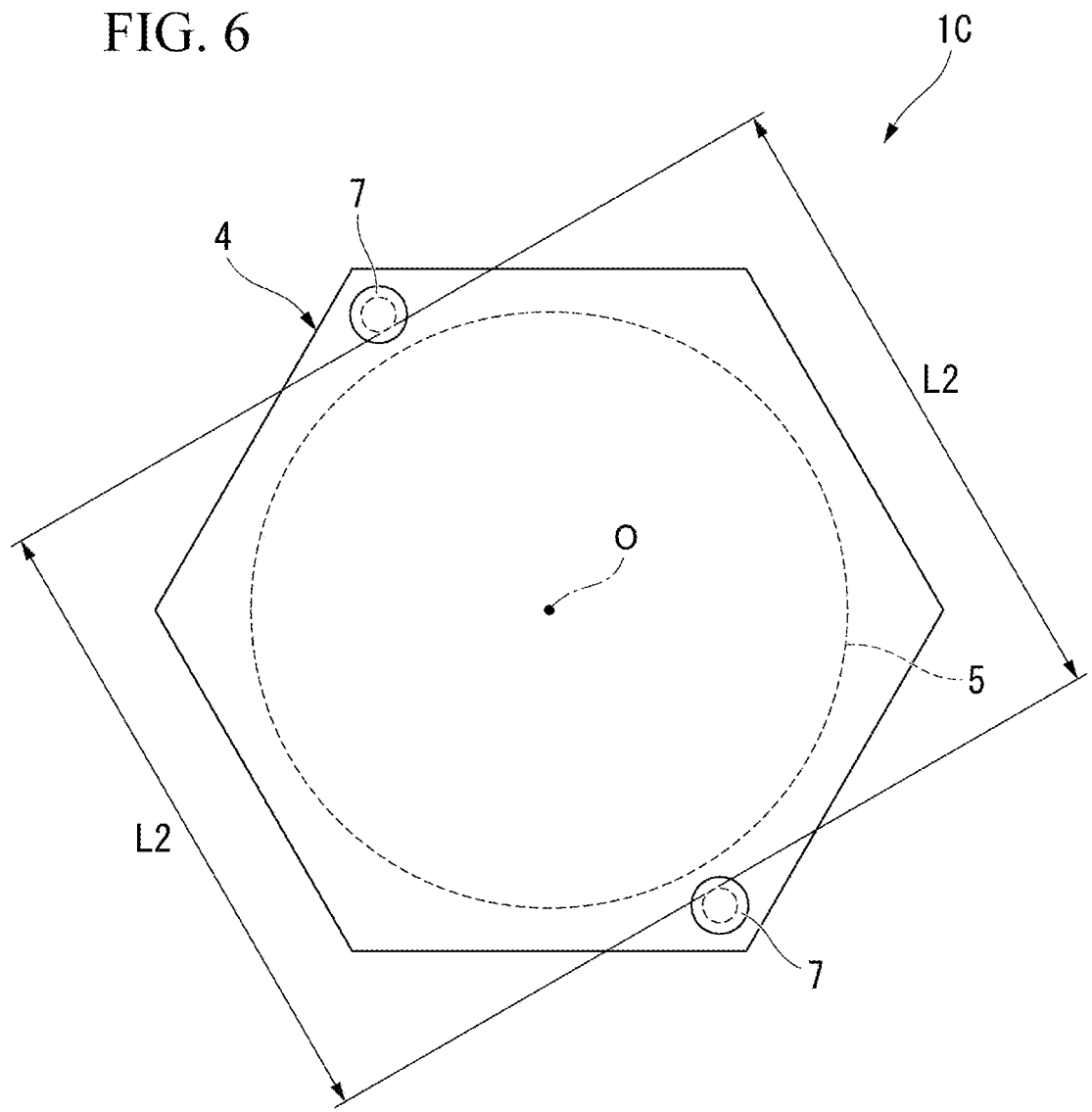
FIG. 6 is a plan view showing an arrangement of conductor portions of a detection device according to a first modification of the second embodiment of the present invention.

In the second embodiment, the case where three conductor portions 7 are provided has been described. However, the number of conductor portions 7 is not limited to three. For example, two conductor portions 7 may be provided in the circumferential direction about the axial line O as in the detection device 1C shown in FIG. 6. In the detection device 1C, when the cover portion 4 is viewed from the axial line O direction, two conductor portions 7 are arranged on each diagonal line of the hexagon. The two conductor portions 7 of the detection device 1C are equally arranged in the circumferential direction about the axial line O. A linear distance L2 between the two conductor portions 7 is $\lambda/4$, and the antenna gain is improved over the entire circumference.

Other Embodiments

Although the embodiment of the present invention has been described above, the present invention is not limited thereto and can be appropriately changed without departing from the technical idea of the invention.

In the second embodiment described above, the case where the cover portion 4 and the main body portion 2 are electrically connected to each other by the conductor portion 7 has been described; however, the main body portion 2 and the cover portion 4 may be connected to each other by a screw formed of an insulating material such as a synthetic resin separately from the conductor portion 7. Further, the main body portion 2 and the cover portion 4 of the first embodiment may be connected to each other using screws made of an insulating material of such a synthetic resin, or the like. In this way, it is possible to increase the connecting strength between the main body portion 2 and the cover portion 4.

Although three conductor portions 7 are provided in the second embodiment and the first modification of the second embodiment, two or more conductor portions 7 may be provided. In addition, when the plurality of conductor portions 7 are provided, the intervals between the conductor portions 7 adjacent to each other in the circumferential direction about the axial line O are equally arranged. However, when uniform antenna gain in all directions around the axial line O is not required, the intervals between the conductor portions 7 does not have to be equal.

In each embodiment, the case where the main body portion 2 has a shape similar to a bolt and is fixed to the through hole H by a screw action has been described. However, the main body portion 2 is not limited to a shape similar to a bolt, and for example, the main body portion 2 may be fixed to the through hole H by welding, adhesion, or the like. Similarly, although the case where the cover portion 4 is formed in a hexagonal shape when seen from plan view has been described, the cover portion 4 may be formed in a shape other than a hexagonal shape as long as the cover portion 4 does not prevent the main body portion 2 from being fixed to the through hole H.

In each embodiment, the case where the oscillation portion 6 causes the slot antenna to function via the wire antenna portion 6B has been described. However, the wire antenna portion 6B may be omitted, and a voltage may be directly applied by wire between the cover portion 4 and the head portion 12 from the circuit board portion 6A, for example, so that wireless output is performed from the slot antenna.

Figure 7:
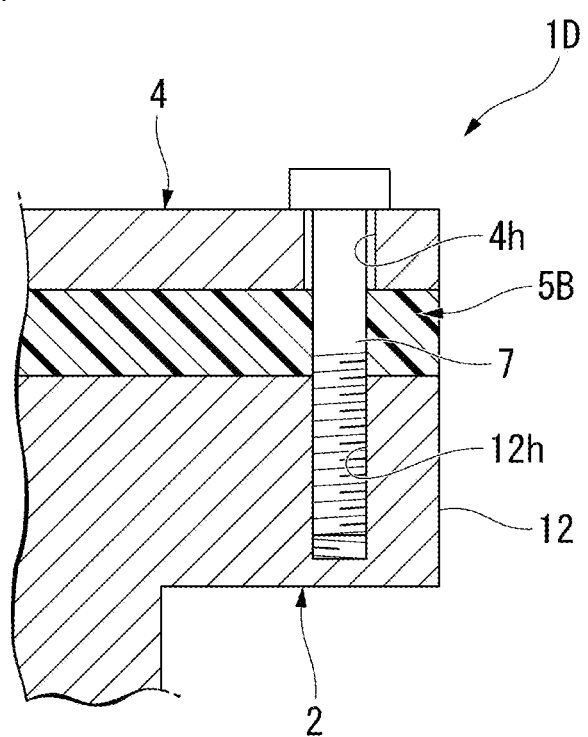
FIG. 7 is a cross-sectional view corresponding to FIG. 4 of a detection device according to modifications of the first and second embodiments of the present invention.

In the first and second embodiments and the first modification of the second embodiment, the gap G between the main body portion 2 and the cover portion 4 is a void space; however, similarly to the screw made of the insulating material described above, a material that does not hinder the operation of the slot antenna may be disposed in the gap G. For example, as shown in FIG. 7, the gap G may be filled with a resin 5B that does not hinder the operation of the slot antenna. FIG. 7 shows the case where the gap G of the second embodiment is filled, but the gaps G in the first embodiment and the first modification of the second embodiment can also be filled with the resin 5B. By filling the gaps G with such a material that does not hinder the operation of the slot antenna, it is possible to prevent dust, moisture, and the like, from entering the inside of the insulating portion 5A. Therefore, it is possible to improve the reliability of the detection devices 1A, 1B, and 1C.

Figure 8:
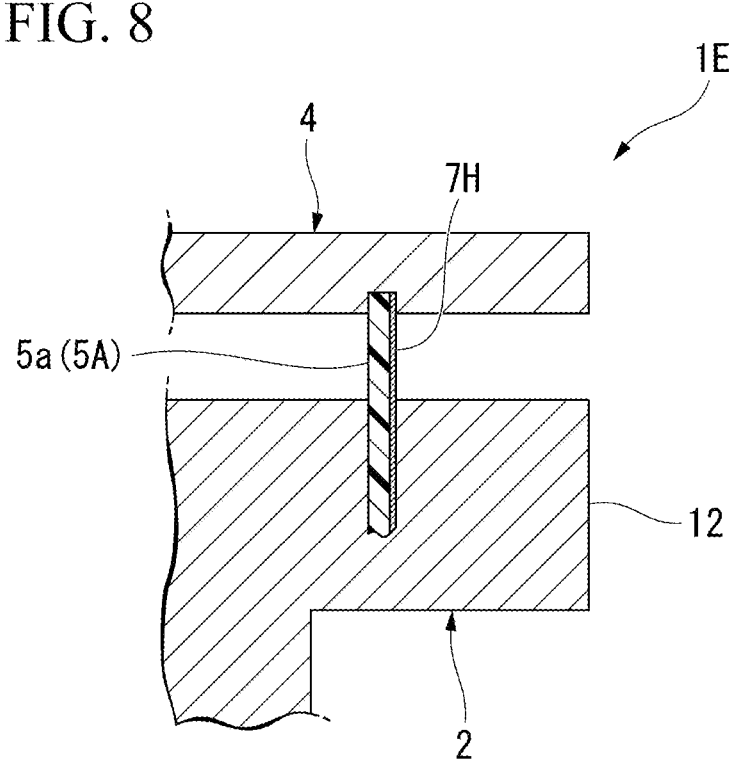
FIG. 8 is a cross-sectional view corresponding to FIG. 4 of a detection device according to a second modification of the second embodiment of the present invention.
Figure 9:
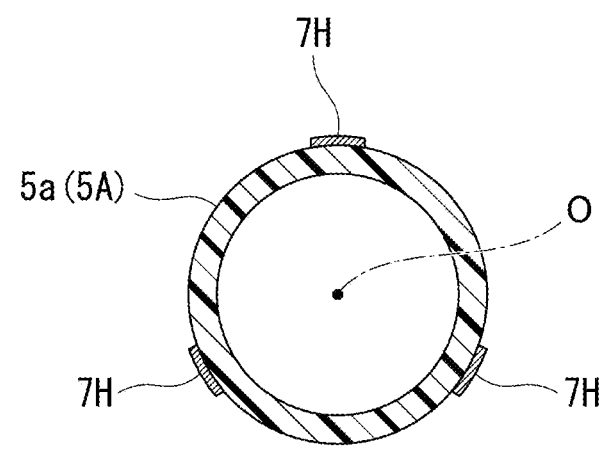
FIG. 9 is a cross-sectional view of conductor portions and an insulating portion, which is orthogonal to an axial line, according to a second modification of the second embodiment of the present invention.

In the second embodiment and the first modification of the second embodiment, the case where the conductor portions 7 are formed of a columnar screw has been described. However, the conductor portions 7 are not limited to a screw, and may be a conductor having another shape. For example, as shown in FIG. 8 and FIG. 9, a conductor portion 7H formed on the outer peripheral surface of the lateral wall 5a of the insulating portion 5A and made of metallic foil or the like for electrically connecting the head portion 12 and the cover portion 4 may be used. Further, the conductor portion 7H made of metallic foil or the like for electrically connecting the head portion 12 and the cover portion 4 may be formed on the inner peripheral surface of the lateral wall 5a of the insulating portion 5A.

INDUSTRIAL APPLICABILITY

According to the present invention, it is possible to prevent a decrease in installation flexibility while wirelessly outputting a detection result.

REFERENCE SIGNS LIST 1A, 1B, 1C, 1D, 1E: Detection Device
2: Main Body Portion
3: Detection Portion
4: Cover Portion
4d: Accommodation Recess
4h: Loose insertion hole
5A: Insulating Portion
5B: Resin
5a: Lateral Wall
6: Oscillation Portion
6A: Circuit Board Portion
6B: Wire Antenna Portion
7, 7H: Conductor Portion
11: Insertion Portion
11t: End Surface
12: Head Portion
12d: Accommodation Recess
12t: End Surface
13: Recessed Portion
15: Light-Emitting Element
16: Light-Receiving Element
G: Gap
H: Through hole
O: Axial Line

The invention claimed is:

1. A detection device that is capable of being attached to a through hole, comprising:
   a main body portion including an insertion portion that is capable of being disposed inside the through hole and a head portion that is disposed outside the through hole when the insertion portion is disposed inside the through hole;
   a detection portion disposed in the insertion portion and configured to detect a state of a fluid;
   a cover portion disposed so as to form a gap between the cover portion and the head portion;
   an insulating portion having a cylindrical lateral wall and disposed so as to be sandwiched between the head portion and the cover portion; and
   an oscillation portion accommodated inside the insulating portion and configured to perform a wireless output of a detection result of the detection portion using the head portion, the cover portion, and the gap as a slot antenna.

2. The detection device according to claim 1,
   wherein a conductor portion that is disposed so as to extend between the main body portion and the cover portion and defines the gap in a circumferential direction about an axial line of the through hole, and
   the conductor portion forms the slot antenna together with the head portion, the cover portion, and the gap.

3. The detection device according to claim 2,
   wherein a plurality of the conductor portions including the conductor portion are provided at intervals in the circumferential direction and are arranged at equal intervals in the circumferential direction.

4. The detection apparatus according to claim 3,
wherein an interval between the conductor portions adjacent to each other in the circumferential direction is $\lambda/4$ with respect to a wavelength $\lambda$ of the wireless output.

5. The detection device according to claim 4,
wherein the conductor portion is a screw member that connects the main body portion and the cover portion to each other.

6. The detection device according to claim 2
wherein the conductor portion is a screw member that connects the main body portion and the cover portion to each other.

7. The detection device according to claim 3,
wherein the conductor portion is a screw member that connects the main body portion and the cover portion to each other.

\* \* \* \* \*